United States Patent [19]
Stern

[11] Patent Number: 5,108,403
[45] Date of Patent: Apr. 28, 1992

[54] BONE WAXING DEVICE

[76] Inventor: Mark S. Stern, 12320 Greens East Rd., San Diego, Calif. 92128

[21] Appl. No.: 611,078

[22] Filed: Nov. 9, 1990

[51] Int. Cl.$^5$ .............................................. A61F 2/32
[52] U.S. Cl. ........................................ 606/93; 606/94
[58] Field of Search ............................ 606/92, 94, 95; 222/391; 604/61, 209; 633/13

[56] References Cited

U.S. PATENT DOCUMENTS

| | | | |
|---|---|---|---|
| 1,523,068 | 1/1925 | Hein | 606/93 |
| 4,338,925 | 7/1982 | Miller | 606/94 |
| 4,405,249 | 9/1983 | Scales | 606/93 |
| 4,546,767 | 10/1985 | Smith | 606/93 |
| 4,751,921 | 6/1988 | Park | 606/93 |
| 4,973,334 | 11/1990 | Ziemann | 606/92 |
| 4,994,065 | 2/1991 | Gibbs | 606/92 |

FOREIGN PATENT DOCUMENTS 8901322  2/1989  World Int. Prop. O. ............ 606/92

Primary Examiner—Robert A. Hafer
Assistant Examiner—Michael Brown
Attorney, Agent, or Firm—Brown, Martin, Haller & McClain

[57] ABSTRACT

The present invention is a device including a hollow tube which contains a supply of beeswax which can be controllably extruded for use. The hollow tube has a plunger-like device mounted at its side or at one end to permit external pressure to be provided to compress the contents of the tube. An opening is located at the end of the tube opposite the plunger through which the wax is extruded. The size of the opening is determined by the size of the bone pore to be filled and the quantity of wax desired. A metal tip is affixed adjacent to the opening for applying the wax to the bone. The length and width of the metal tip is determined by the size of the bone pore to be filled. A single hollow tube may be used for two different size applicators by dividing the tube with a partition to form two chambers, each of which is filled with beeswax.

4 Claims, 1 Drawing Sheet

BONE WAXING DEVICE

BACKGROUND OF THE INVENTION

Many types of surgery, including orthopedic and neurosurgery, require cutting through bone to gain access to the surgical site. Bone is a porous material containing numerous blood vessels; in compact bone the blood vessels are in the Haversian canals and in the spongy bone they are in large spaces which contain the marrow. For purposes of this disclosure, the openings in the bone containing the blood vessels will be referred to as "pores". Cutting the bone causes a substantial amount of bleeding, management of which must be achieved before proceeding further with the surgery. The most common technique for minimizing the blood loss from the cut bone is to fill the bone pores containing the blood vessels with beeswax. This procedure uses any of a number of spoon or spatula-like devices of various sizes (depending on the pore size to be filled) which a surgical assistant dips into a container of wax, scooping out a small amount of wax. The surgical assistant hands the device to the surgeon who directly applies the wax to the bone pore. The surgeon returns the device to the assistant who prepares another application of wax, repeating the procedure until all bone pores along the incision are filled to prevent further bleeding so the surgeon can proceed with the operation. The process of handing the instrument back-and-forth between the assistant and the surgeon is tedious and time consuming, as well as providing opportunity for dropping the device.

It would therefore be desirable to provide an apparatus for applying beeswax to surgically cut bone to inhibit bleeding which does not require repeated reloading or handling of an applicator. It is to such apparatus that the present invention is directed.

SUMMARY OF THE INVENTION

The present invention is a device which contains a supply of beeswax which can be controllably extruded for use. The device has at least one chamber for storing beeswax, an opening at the end of the chamber through which the wax may be extruded, means for controllably forcing a quantity of wax through the opening and an applicator tip adjacent to the opening for pressing the wax into the bone pore when the wax is presented through the opening.

In an exemplary embodiment, the device comprises a hollow tube which has a plunger-like device mounted at its side or at one end to permit external pressure to be provided to compress the contents of the tube. An opening is located at the end of the tube opposite the plunger through which the wax is extruded. The size of the opening is determined by the size of the bone pore to be filled and the quantity of wax desired. A metal tip is affixed adjacent to the opening for applying the wax to the bone. The length and width of the metal tip is determined by the size of the bone pore to be filled.

A single hollow tube may be used for two different size applicators by dividing the tube with a partition to form two chambers, each of which is filled with beeswax. One plunger is provided for each chamber to force the wax out of the respective openings. For applications to large bone pores, the first chamber has an opening which is relatively large with the corresponding applicator tip being short and wide. The second chamber has a smaller opening with an applicator tip which is long and narrow for use on smaller bone pores where greater accuracy is required.

Generally, the tube of which an applicator is formed is the diameter and length similar to that of a ballpoint pen so that it is easily held and manipulated.

BRIEF DESCRIPTION OF THE DRAWINGS

A better understanding of the present invention will be provided by consideration of the following detailed description of the preferred embodiments of the present invention, taken in conjunction with accompanying drawings, in which like reference numerals refer to like parts and in which.

DETAILED DESCRIPTION OF THE PREFERRED EMBODIMENT

Figure 1:
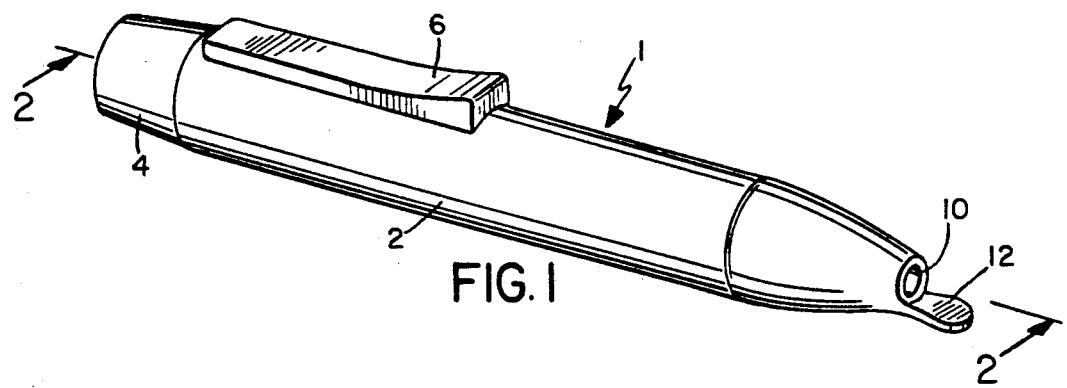
FIG. 1 is a perspective view of an applicator according to the present invention.
Figure 2:
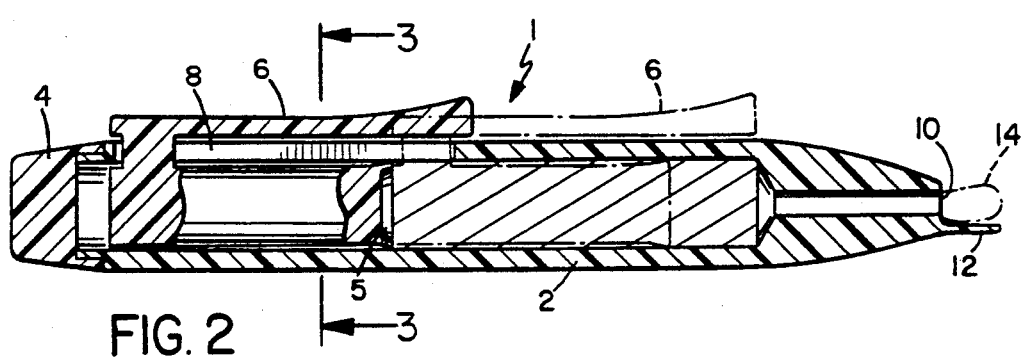
FIG. 2 is a cross-sectional view taken along line 2—2 of FIG. 1.

A first embodiment of the bone waxing device 1 is shown in FIGS. 1 and 2 as a hollow tube 2 which has a plunger 5 attached to an external handle 6 through opening 8 in the side of tube 2. A cap 4 is attached on the end to permit filling. An opening 10 is disposed at the dispensing end of the tube 2 and an applicator tip 12 is attached adjacent to opening 10. Wax 14, usually beeswax, is stored in the device 1.

Tube 2 may be made from plastic, metal, glass or any similar rigid or semi-rigid material which may be formed in a tubular shape. A semi-rigid plastic may be used for a tool which conforms to hand shape or individual comfort. A transparent plastic is preferred for its durability, economy, and to permit monitoring of the quantity of wax remaining in the tube.

Plunger 5 consists of a plate on the interior of tube 2 which presses against a broad surface of the wax 14, placing sufficient compressive force on the wax 14 to cause a portion of it to be extruded through opening 10. External handle 6 is the controller by which plunger 5 is activated to dispense the wax. The plunger 5 and external handle 6 may be formed as a single unit or as two pieces joined together through the opening 8. Suggested materials are metal such as stainless steel or rigid plastic similar to that used for tube 2. Opening 8 may be a single slot along which external handle 6 may be slid, or it may be multiple holes through which pins connecting handle 6 to plunger 5 extend. In the latter case, as shown in FIG. 4, the user will press inward on the handle 26 or 26' which extends through holes 28 to cause plunger 27 or 27' to compress the wax to be extruded.

Opening 10 is the orifice through which the wax 14 is extruded. The size of opening 10 is determined by the quantity of wax to be dispensed which in turn is determined by the size of the bone pore to be filled. For larger pores, a thicker stream of wax is desired. For smaller pores, a thin stream of wax is more suitable to form a smaller plug.

Associated with the different sizes for opening 10 will be the applicator tip 12. For the larger opening 10, a broad, short tip is desirable to apply a relatively large plug of wax to a larger pore. For a smaller opening 10, a long, narrow tip provides better accuracy for application to a small pore.

Figure 4:
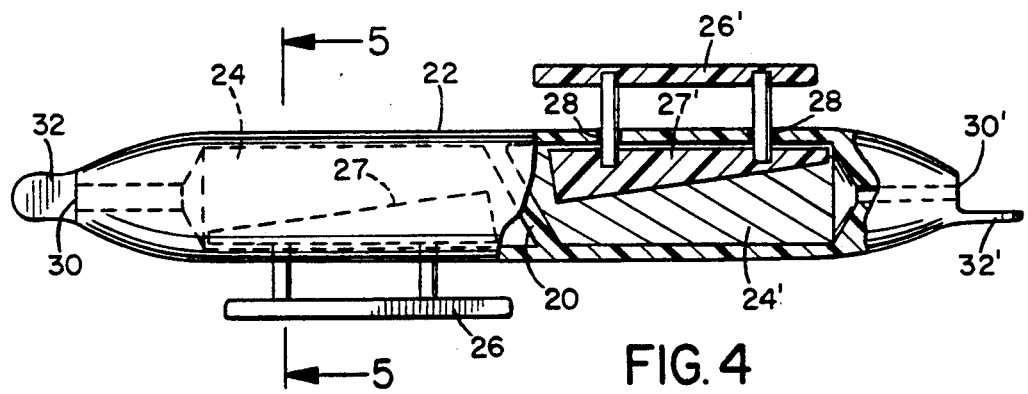
FIG. 4 is a side elevation view of a dual applicator, partially cut away.
Figure 3:
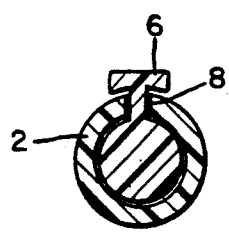
FIG. 3 is a cross-sectional view taken along line 3—3 of FIG. 2.
Figure 5:
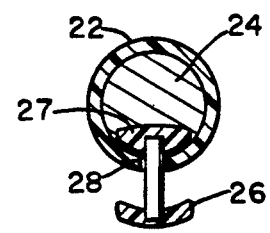
FIG. 5 is a cross-sectional view taken along line 5—5 of FIG. 4.

In a second embodiment shown in FIG. 4, a dual applicator is made possible by inserting a partition 20 across the tube 22, thereby creating two separate chambers 24 and 24'. One plunger/external handle combination, either 26/27 or 26'/27', is provided for each chamber.

Corresponding to chamber 24 is a relatively large opening 30 for application of wax to fill larger bone pores. Adjacent to opening 30 is applicator tip 32 which is broad and short.

Chamber 24' feeds through small opening 30' to dispense relatively small quantities of wax for application to smaller bone pores. Applicator tip 32' is long and narrow for more accurate application.

Ideally, the bone waxing device is the general shape and size of a ballpoint pen or similar implement which is easily hand-held and manipulated. The device is also disposable in the preferred embodiment so that, rather than trying to refill the chamber after it is emptied, the device is discarded and a new one is made available for use. This configuration can be inexpensively produced enabling the concept of disposability of the device.

The bone waxing device of the present invention is inexpensive, easily manipulated and saves time and effort during surgery to provide more efficient use of the surgeon's and the surgical assistant's skills.

It will be evident that there are additional embodiments which are not illustrated above but which are clearly within the scope and spirit of the present invention. The above description and drawings are therefore intended to be exemplary only and the scope of the invention is to be limited solely by the appended claims.

I claim:

1. A device for applying a sealant to a bone pore for inhibiting bleeding when surgically cutting through bone, said device comprising:

a hollow tube having a partition therein defining a first chamber and a second chamber, said first chamber having a first opening at its end, said first opening having a first diameter and said second chamber having a second opening at its end, said second opening having a second diameter, said first diameter being larger than said second diameter for dispensing a wider stream of sealant than is dispensed by said second opening;

a plunger means corresponding to each said chamber for placing a compressive force upon said sealant;

an applicator tip adjacent to each said opening for applying said sealant extruded from said opening to said bone pore.

2. A device as in claim 1 wherein a first applicator tip is adjacent to said first opening and a second application tip is adjacent to said second opening, said first applicator tip being broad and short relative to said second applicator tip.

3. A method of applying a sealant to a bone pore for inhibiting bleeding when surgically cutting through the bone which comprises:

selecting a hollow tube with at least one chamber and an opening at an end of each said chamber;

filling each said chamber of said hollow tube with said sealant;

inserting a plunger in each said chamber for placing a compressive force upon said sealant whereby said sealant may be extruded through said opening;

attaching an applicator tip adjacent to said opening;

compressing said plunger;

dispensing a desired amount of said sealant through said opening; and pressing said applicator tip against said dispensed sealant to force said dispensed sealant into said bore pore.

4. A method as in claim 3 further comprising inserting a partition within said hollow tube whereby a first chamber and a second chamber are formed.

* * * * *